US008247560B2

(12) United States Patent
De Vries et al.

(10) Patent No.: US 8,247,560 B2
(45) Date of Patent: *Aug. 21, 2012

(54) TRISUBSTITUTED 3,4-DIHYDRO-1H-ISOQUINOLIN COMPOUND, PROCESS FOR ITS PREPARATION, AND ITS USE

(75) Inventors: Maria Andreas Hendrikus De Vries, Maastricht (NL); Doris Domin, Vienna (AT); Matthias Helms, Linz (AT); Christoph Imboden, Hofstetten (CH); Ralph Koberstein, Lorrach (DE); Zarghun Nazir, Linz (AT); Wolfgang Skranc, Vienna (AT); Michael Stanek, Linz (AT); Wilhelm Tschebull, Linz (AT); Maria Gerardus Karel Verzijl, Well (NL); Jurgen Stichler, Riehen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 488 days.

This patent is subject to a terminal disclaimer.

(21) Appl. No.: 12/497,023

(22) Filed: Jul. 2, 2009

(65) Prior Publication Data

US 2010/0010226 A1 Jan. 14, 2010

Related U.S. Application Data

(63) Continuation-in-part of application No. PCT/IB2008/055509, filed on Dec. 23, 2008.

(30) Foreign Application Priority Data

Dec. 28, 2007 (WO) .................. PCT/IB2007/055334

(51) Int. Cl.
C07D 217/20 (2006.01)
(52) U.S. Cl. ....................................................... 546/149
(58) Field of Classification Search .................. None
See application file for complete search history.

(56) References Cited

U.S. PATENT DOCUMENTS

| 3,480,714 | A | 11/1969 | Werner |
| 6,703,392 | B2 | 3/2004 | Aissaoui et al. |
| 7,192,950 | B2 | 3/2007 | Aissaoui et al. |
| 2009/0082394 | A1 | 3/2009 | Jenck |

FOREIGN PATENT DOCUMENTS

| DE | 204917 | 12/1983 |
| DE | 258817 | 8/1988 |
| DE | 261158 | 10/1988 |
| EP | 0 916 637 | 5/1999 |
| EP | 1 288 202 | 3/2003 |
| JP | 61 053268 | 3/1986 |
| JP | 07 267961 | 10/1995 |
| JP | 10 095766 | 4/1998 |
| WO | WO-00/37478 A1 | 6/2000 |
| WO | WO 01/68609 | 9/2001 |
| WO | WO 02/051838 | 7/2002 |
| WO | WO 03/002559 | 1/2003 |
| WO | WO 03/051871 | 6/2003 |
| WO | WO 2004/085403 | 10/2004 |
| WO | WO-2004/085403 A1 | 10/2004 |
| WO | WO-2005/118548 A1 | 12/2005 |
| WO | WO-2006/003194 A1 | 1/2006 |
| WO | WO 2007/105177 | 9/2007 |
| WO | WO 2007/122591 | 11/2007 |

OTHER PUBLICATIONS

Brisbare-Roch, C. et al., "Promotion of sleep by targeting the orexin system in rats, dogs and humans." Nat. Med. (2007), 13, 150-155.
T. Ireland et al. in Angew. Chem. J. Int. Ed. (1999), 38, 3212.
Fukuzawa, et al. "Preparation of Chiral Homoannularly Bridged N,P-Ferrocenyl Ligands by Intramolecular Coupling of . . . ". Eur. J. Org. Chem. (2007), 5540-5545.
T. Ireland et al. in Angew. Chem. J. Int. Ed. (2008), 47, 3666.
N. Uematsu et al., "Asymmetric Transfer Hydrogenation of Imines." Journal of the American Chemical Society, vol. 118, 1996, pp. 4916-4917.
Spindler F. et al., "Modular chiral ligands: the profiling of the . . . ". Tetrahedron Asymmetry, Pergamon Press Ltd., Oxford, GB vol. 15, No. 14, Jul. 26, 2004, pp. 2299-2306.
J.G de Vries, C.J., Elsevier, Eds.; Handbook of Homogenous Hydrogenation. Wiley, 2007, Ch. 23-25.
Zhao Yujun et al. Database Caplus, Chemical Abstracts Service, Columbus , 2005.
Gould, P., "Salt Selection for Basic Drugs", International Journal of Pharmaceutics, vol. 33, pp. 201-217, (1986).
Hutchins, et al., "Solid Phase Synthesis of Tetrahydroisoquinolines and Tetrahydroimidazopyridines", Tetrahedron Letters, vol. 37, pp. 4865-4868, (1996).
Koberstein, R., et al., "Tetrahydroisoquinolines as Orexin Receptor Antagonists: Strategies for Lead Optimization by Solution-Phase Chemistry", Chimia 57, pp. 270-275, (2003).
Li et al, "Asymmetric Hydrogenation of Cyclic Imines with an Iconic Cp*Rh(III) Catalyst"; J. Am. Chem. Soc., 2008, 130, 13208-13209.
Stahl, et al., Handbook of Pharmaceutical Salts, Wiley-VCH, Weinheim, Zurich, pp. 329-350, (2002).

*Primary Examiner* — Zinna Northington Davis
(74) *Attorney, Agent, or Firm* — Hoxie & Associates LLC

(57) ABSTRACT

The present invention relates to the compound of formula 7*acetate (see below), a process for its preparation, and its use

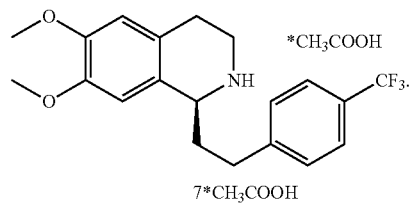

10 Claims, No Drawings

TRISUBSTITUTED 3,4-DIHYDRO-1H-ISOQUINOLIN COMPOUND, PROCESS FOR ITS PREPARATION, AND ITS USE

CROSS REFERENCE TO RELATED APPLICATIONS

This application is a continuation-in-part of PCT Application No. PCT/IB2008/055509, filed, Dec. 23, 2008, which claims the benefit of PCT/IB2007/055334, filed Dec. 28, 2007, the contents of each of which are incorporated herein by reference.

The present invention relates to a compound of formula 7*acetate (see below), a process for its preparation, and its use for the preparation of the compound of formula I.

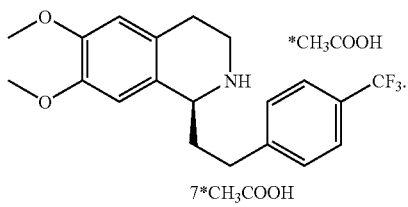

7*CH₃COOH

Further, the present invention relates to a new process for the preparation of almorexant hydrochloride, i.e. the tetra-substituted 3,4-dihydro-1H-isoquinoline compound of formula I*HCl, and new intermediates.

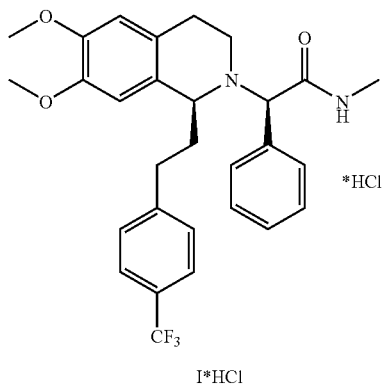

I*HCl

Almorexant is known from WO 2005/118548 and *Nat. Med.* (2007), 13, 150-155 and is especially useful as orexin receptor antagonist. It can be obtained through a multiple-step synthesis. The key-intermediate in the synthesis of almorexant is the 1-substituted 3,4-dihydro-1H-isoquinoline derivative of formula 7. Accordingly, almorexant can be prepared by cyclisation of N-phenethyl-propionamide with POCl₃, followed by enantioselective transfer hydrogenation in the presence of a chiral Ru(II)-complex leading to the compound of formula 7, and coupling of the latter with the corresponding tosylate.

A family of asymmetric ferrocenyl hydrogenation catalysts such as transition metal complexes with the commercially available Taniaphos-ligand (S)-1-dicyclohexylphosphino-2-[(S)-α-(dimethylamino)-2-(dicyclohexylphosphino)benzyl]-ferrocene (that is presently still incorrectly described as the (R)-1-dicyclohexylphosphino-2-[(S)-α-(dimethylamino)-2-(dicyclohexylphosphino)benzyl]-ferrocene in the commercial catalogue) was first described by T. Ireland et al. in *Angew. Chem. J. Int. Ed.* (1999), 38, 3212, although with an incorrect absolute configuration regarding the ferrocenyl group that was believed to be (S) instead of (R). Similar compounds were disclosed shortly afterwards in WO00/37478. Years later, Fukuzawa et al. (*Eur. J. Org. Chem.* (2007), 5540-5545) demonstrated that the ferrocenyl configuration reported in the article of T. Ireland et al. was incorrect and that the absolute configuration of the ferrocenyl group was actually (R) and not (S), after which a corresponding corrigendum was published by T. Ireland et al. (*Angew. Chem. J. Int. Ed.* (2008), 47, 3666).

It has now surprisingly been found that compound of formula 7*acetate has improved properties over the HCl analogue, and that compound of formula I can be manufactured in an improved way by the process of the present invention which uses asymmetric ferrocenyl hydrogenation catalysts similar to those first described by T. Ireland et al. Further surprising technical effects are described in the description.

Various embodiments of the invention are presented hereafter:

i) the compound of formula 7*acetate

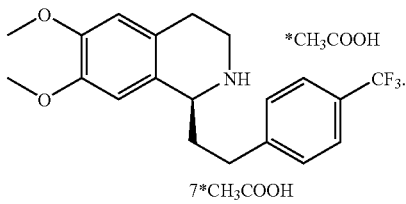

7*CH₃COOH ii) a process for the preparation of the compound of formula 7*acetate

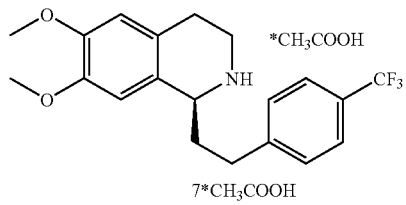

7*CH₃COOH which process comprises the reaction of the compound of formula 7

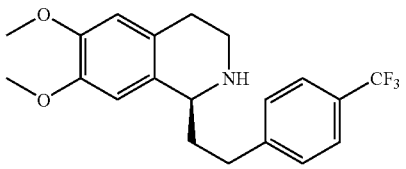

with acetic acid, to obtain the compound of formula 7*acetate.

iii) a process according to embodiment ii), for the preparation of the compound of formula 7*acetate, characterized in that the compound of formula 7

 7

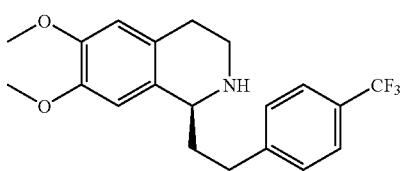

is prepared by hydrogenation of the compound of formula 4

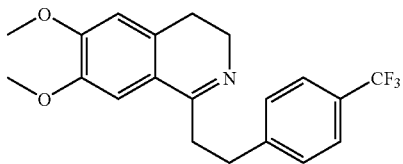

in the presence of bis[chloro-1,5-cyclooctadiene-iridium], (S)-1-dicyclohexylphosphino-2-[(S)-α-(dimethylamino)-2-(dicyclohexylphosphino)benzyl]-ferrocene, iodine and a solvent, under hydrogen pressure of 1-200 bar, to obtain the compound of formula 7.

iv) a process according to embodiment ii) or iii), for the preparation of the compound of formula 7*acetate, characterized in that the compound of formula 4

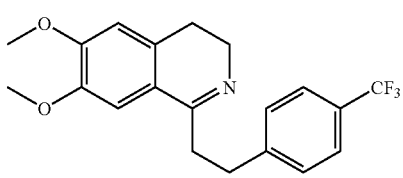

is prepared by reaction of the compound of formula 4*mesylate

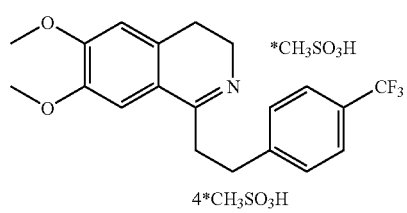

4*CH$_3$SO$_3$H with a base, to obtain the compound of formula 4.

v) a process according to embodiment ii), wherein the reaction is carried out with 0.9 to 1.3 equivalents of acetic acid.

vi) a process according to embodiment iii), wherein the amount of iodine compared to the amount of Ir is between 0.2 and 10 mol equivalents.

vii) a process according to embodiment iii) or vi), wherein the molar ratio between Ir and the chiral ligand is between 0.5:1 and 1:0.5.

viii) a process according to one of embodiments iii), vi) and vii), wherein the hydrogen pressure is between 1 and 50 bar.

ix) a process according to embodiment iv), wherein the amount of base is between 0.9 and 1.5 mol equivalents.

x) the use of compound of formula 7*acetate

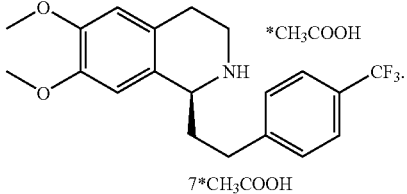

for the preparation of the compound of formula I*HCl

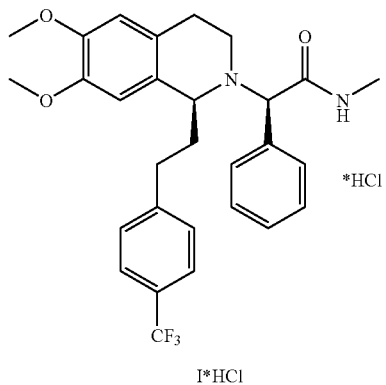

The following paragraphs provide definitions of the various chemical moieties for the compounds according to the invention or of other terms used herein and are intended to apply uniformly throughout the specification and claims, unless an otherwise expressly set out definition provides a different definition:

The term "C$_{1-4}$ aliphatic alcohol" as used herein denotes straight or branched chain alkyl residues containing 1 to 4 carbon atoms with one hydroxy group, such as methanol, ethanol, propanol, isopropanol, butanol, isobutanol or tert.-butanol. Preferred C$_{1-4}$ aliphatic alcohols are methanol or ethanol.

The term "C$_{4-8}$ aliphatic hydrocarbon" as used herein denotes to straight or branched chain aliphatic hydrocarbons containing 4 to 8 carbon atoms, such as butane, isobutane, tert.-butane, pentane, hexane, heptane or octane. The corresponding isomers are also encompassed by the term "C$_{4-8}$ aliphatic hydrocarbon".

Whenever the symbol "*" is followed by the expression "acetate", "mesylate", "HCl", "CH$_3$SO$_3$H" or "CH$_3$COOH", it denotes the corresponding salt of the compound after which this combination is placed. For example, the expression "the compound of formula 7*acetate" denotes the acetate salt of the compound of formula 7.

The abbreviations "ee", "mol %", "wt %" and RT refer respectively to the enantiomeric excess of an enantiomeric mixture, to the molar percentage of a mixture, to the weight percentage of a mixture and to room temperature.

The abbreviations "Ac" and "MIBK" refer respectively to the acetyl group and to methylisobutylketone. "IPA" refers to isopropanol, "MTBE" refers to methyl-tert.-butyl-ether, "DCM to dichloromethane, "EtOAc" to ethylacetate.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, the denomination 3,4-dihydro-1H-isoquinoline (as used herein e.g. for compounds of formula 7 or 1) and the denomination 1,2,3,4-tetrahydroisoquinoline as used herein refer to the same structural entity.

The present invention is further described by reaction schemes 1-5.

Reaction scheme 1:

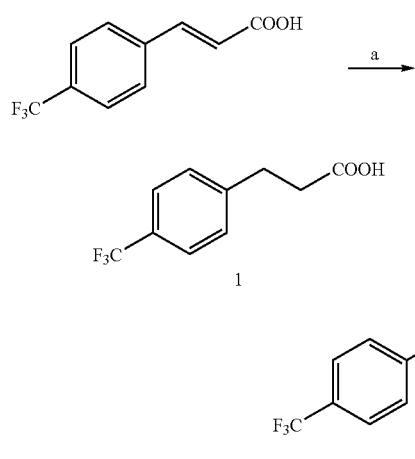

In step a of the reaction, commercially available 4-trifluoromethylcinnamic acid is hydrogenated in the presence of Pd/C to obtain compound of formula I. Appropriate solvents are $C_{1-4}$ aliphatic alcohols and mixtures of $C_{1-4}$ aliphatic alcohols with water. Preferred solvent is methanol. The hydrogenation may be carried out between 0.9 to 15 bar, preferably at 2 bar, in the presence of 0.1 to 5 wt % (notably 0.15 to 5 wt %) of a 5% Pd/C catalyst (preferably 2 wt % Pd/C, having 5% Pd on charcoal).

The reaction is carried out at a reaction temperature between 0° C., up to the corresponding boiling point of the respective solvent used, preferably between 15 to 50° C. (notably 15 to 25° C.).

In step b of the reaction, the compound of formula 1 is reacted with methanol in the presence of an acid (such as p-toluene sulfonic acid, methanesulfonic acid or sulfuric acid, preferably in the presence of sulfuric acid) to obtain the corresponding ester of formula 2. Preferably, the reaction is carried out in the presence of 5 mol % $H_2SO_4$, at a reaction temperature between 50 to 110° C. (notably 50 to 80° C.) (preferably at the boiling point of the mixture). In a preferred embodiment of the reaction, the compound of formula 1 is not isolated after step a (only the catalyst is removed by filtration), and the reaction is continued with step b.

The technical advantage of step b, compared to the prior art, is that it combines two chemical steps.

Reaction scheme 2:

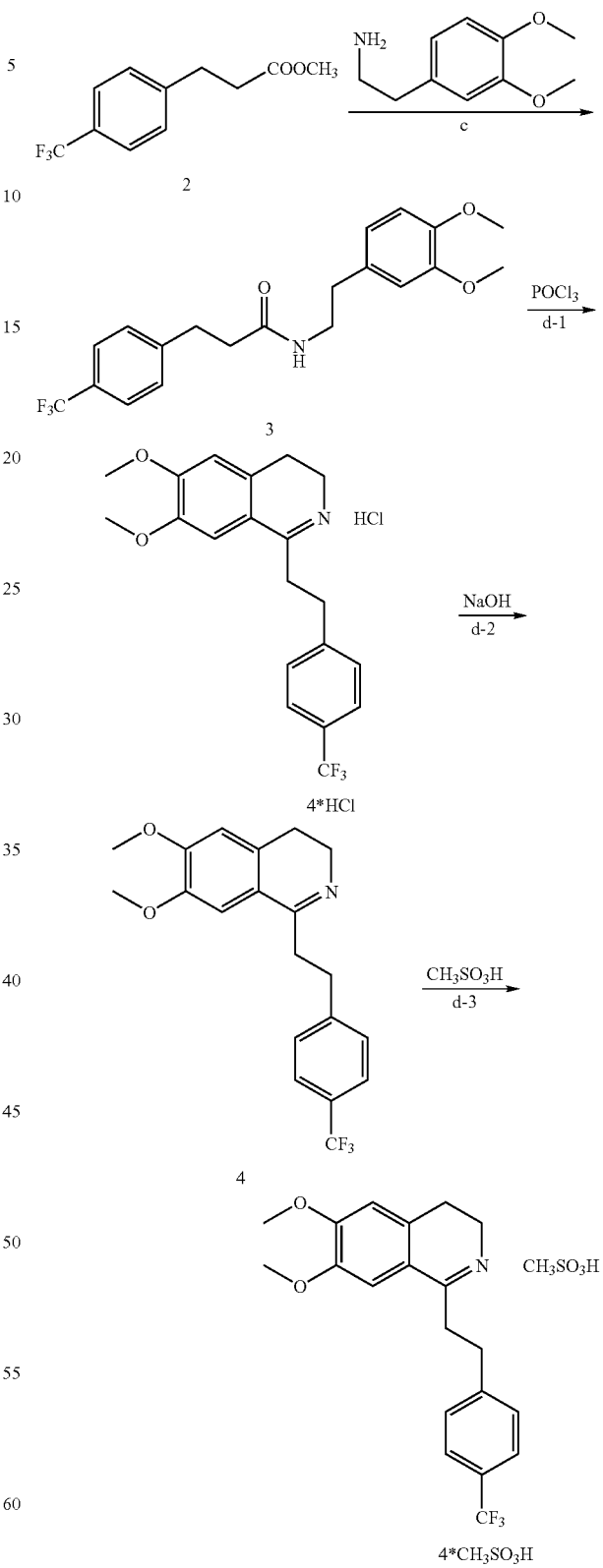

In step c of the reaction, compound of formula 2 is reacted with commercially available 2-(3,4-dimethoxy-phenyl)-ethylamine in the presence of an alcoholate, to obtain the compound of formula 3. Appropriate solvent for the reaction are aromatic boiling solvents (such as benzene or a xylene), aliphatic hydrocarbons which are able to have an azeotrope with the corresponding alcohol (for example heptane). A preferred solvent is toluene. The reaction is carried out at a reaction temperature between 70 to 115° C., preferably at 110° C., in another embodiment preferably at 100° C. Suitable alcoholates (or alkoxides) are those formed by the substitution of the hydrogen atom of the hydroxy group of an alcohol by a metal atom. A preferred alcohol is the one used for the ester, and preferred metal atoms are Na, K or Li. An especially preferred alcoholate (or alkoxide) is sodium methoxide (preferably dissolved in methanol, such as 30% sodium methoxide in methanol).

The technical advantage of step c, compared to the prior art, is that the reaction is more stable, economical (direct coupling to the product; and no expensive coupling reagent is needed) and easy regarding the work up leading to the product.

In step d-1 of the reaction, the compound of formula 3 is reacted in the presence of polyphosphoric acid or phosphorus oxychloride (preferably phosphorus oxychloride in an amount of 0.5 to 1.5 equivalents (notably 1 to 1.5 equivalents), in another embodiment 0.7 to 1.0 equivalents, per equivalent of compound of formula 3) to obtain the compound of formula 4*HCl (said compound is a mixture of phosphorus imine salts and/or chlorophosphorous imine salts). Suitable solvents are aromatic solvents such as benzene, xylene, mesitylene, or toluene (preferably toluene), and a suitable reaction temperature is between 60 to 120° C. (notably 80-100° C.) (preferably 80-110° C.).

In step d-2 of the reaction, the reaction mixture of step d-1 is reacted with a solution of an alkaline hydroxide (preferably a sodium hydroxide solution), to obtain the compound of formula 4.

In step d-3 of the reaction, the reaction mixture of step d-2 is reacted with methanesulfonic acid (preferably 0.9-1.5 equivalents; particularly 1.0-1.2 equivalents) to obtain the compound of formula 4*mesylate. The reaction is carried out at a reaction temperature from −5 to 60° C. (notably −5 to 40° C.), preferably between 0 to 40° C., in another embodiment preferably 0 to 10° C. Suitable solvent systems for the crystallization of compound 4*mesylate are aromatic solvents (notably toluene) and ketones (notably acetone) as well as mixtures thereof.

The compound of formula 4*mesylate is novel over the HCl analogue.

The technical advantages of step d-3, compared to the prior art, are the following:
  As the enantioselective hydrogenation is highly sensitive towards impurities, high purity of the reactants is essential. The surprising advantage of the 4*mesylate compound (as compared to the HCl analogue) is that it precipitates in high purity, notably from solvents like toluene, acetone or mixtures thereof. As a consequence, the 4*mesylate can be subjected directly as free amine into the enantioselective hydrogenation.
  There is only one precipitation and isolation necessary yielding to good product quality, and improvement of the process and reduction of unit steps is achieved.

Additionally, the synthesis of main chain part 1 (reaction schemes 1 and 2) was improved by reducing the number of solvents used.

Reaction scheme 3:

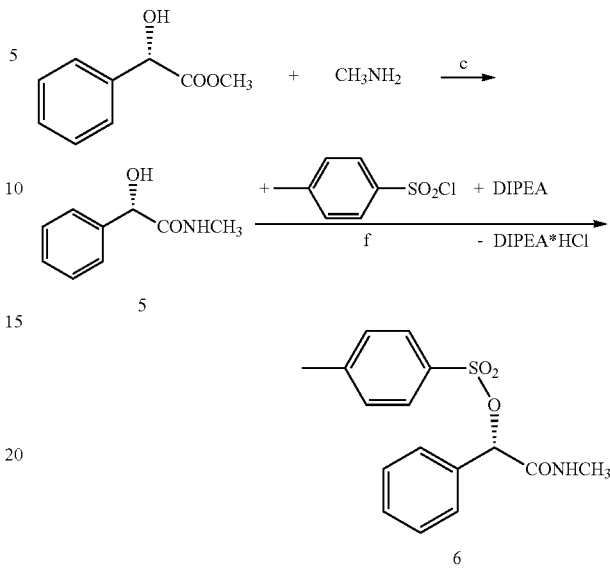

In step e of the reaction, commercially available methylamine is reacted with commercially available methyl (S)-mandelate to obtain the compound of formula 5. In a preferred embodiment, the reaction is carried out with 3 to 5 equivalents of methylamine (preferably 3.8 equivalents), and said methylamine is 30% in aqueous solution. The reaction is carried out at a reaction temperature from 5 to 35° C., preferably from 15 to 25° C. Alternatively, the reaction temperature may be from −5 to 35° C., preferably from 0 to 10° C. After the reaction has been judged complete, excess methylamine may for example be distilled off at reduced pressure.

In step f of the reaction, the compound of formula 5 is reacted with p-toluene sulfonic acid chloride in the presence of a base such as triethylamine, pyridine or N-ethyldiisopropylamine (preferably N-ethyldiisopropylamine), to obtain the compound of formula 6. Alternatively, a base like sodium hydroxide (preferably aqueous sodium hydroxide) may be used.

In a preferred embodiment of the invention, after a solvent switch to ethyl acetate the solution is concentrated, cooled to −2° C. and the precipitate is filtered. Alternatively, toluene may be used in the above procedure and the solution is cooled to −5 to 30° C. (notably 0 to 10° C.).

In a further preferred embodiment, the reaction is carried out with 1.0 to 1.5 equivalents of p-toluene sulfonic acid chloride (preferably 1.0 equivalent), and 1.05 to 3 equivalents of N-ethyldiisopropylamine (preferably 1.1 equivalents).

Suitable solvents are halogenated solvents, such as $CHCl_3$, $CCl_4$, dichloroethane, or dichloromethane (preferably dichloromethane).

The reaction is carried out at a reaction temperature from 0 to 35° C. (notably 5 to 30° C.), preferably below 25° C.

The technical advantages of step f, compared to the prior art, are the following:
  The coupling reaction was improved.
  The overall process was improved with respect to product quality.

Reaction scheme 4:

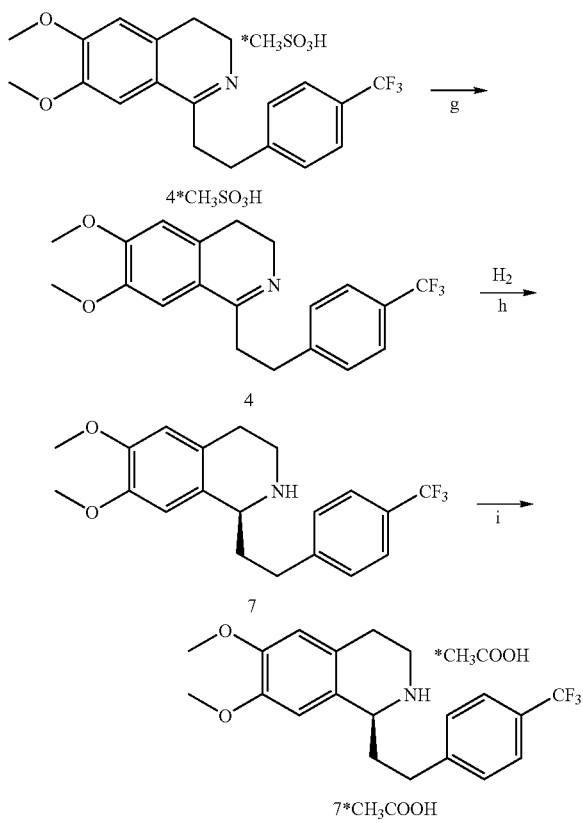

In step g of the reaction, the compound of formula 4*mesylate is reacted with a base (preferably an inorganic base such as sodium hydrogenocarbonate or sodium hydroxide, more preferably sodium hydroxide, especially an aqueous solution of sodium hydroxide) to obtain the compound of formula 4. The amount of base for step g of the reaction may be used in large ranges. Preferably, between 0.9 and 1.5 mol equivalents of the corresponding base is used. Suitable solvents are any organic solvents (preferably a non-protic solvent; more preferred will be a solvent which is used for the following step h, or following steps h-1). Preferred solvents are $C_{1-4}$-alkyl acetates (wherein $C_{1-4}$-alkyl is methyl, ethyl, propyl, isopropyl, butyl, isobutyl or tert.-butyl, preferably methyl or ethyl, and most preferably ethyl). The reaction is carried out at a reaction temperature between −10° C. and 80° C., preferably between 10° C. and 50° C., and more preferably between 15° C. and 35° C. According to a preferred embodiment, activated charcoal (e.g. in an amount of up to 100 g per kg of compound of formula 4*mesylate) is added to the reaction mixture and removed (e.g. by filtration) once the treatment is completed.

In step h of the reaction, the compound of formula 4 is hydrogenated using hydrogen gas or a hydrogen transfer compound (e.g. isopropanol) in the presence of a chiral catalyst (chiral hydrogenation catalyst or transfer hydrogenation catalyst) and a solvent, and optionally in the presence of an additive, to yield the compound of formula 7.

Said catalysts are commercially available, prepared beforehand, or prepared in situ, from any commercially available Ru, Ir and Rh complex (also known as precursors), and a commercially available chiral ligand, chiral ligands, or a combination of different ligands, of which one has to be chiral. Suitable precursors are for example bis(2-methylallyl)(1,5-cyclooctadiene)Ruthenium, [RuCl$_2$(p-cymene)]$_2$, bis(1,5-cyclooctadiene)Iridium tetrafluoroborate, bis[chloro-1,5-cyclooctadiene-iridium], and bis(cyclooctadiene)Rhodium tetrafluoroborate. Preferred precursors are Ir-based precursors (Ru-based and Ir based precursors for the transferhydrogenation).

Suitable chiral ligands are known by the person skilled in the art, and are for example described in the Handbook of Homogeneous Hydrogenation, J. G de Vries, C. J., Elsevier, Eds.; Wiley, 2007, chapter 23-35. Preferred chiral ligands are chiral bisphosphine ligands, and chiral monodentate phosphor containing ligands, amines, aminoalcohols or bisamines.

Suitable chiral ligands are for example the bisphosphines, such JosiPhos type ligands; MandyPhos; TaniaPhos type of ligands; BINAP, and its analogues, DUPhos; Chiraphos; and monodentate ligands such the MonoPhos type ligands, for example (3,5-dioxa-4-phosphacyclohepta[2,1-a;3,4-a']dinaphthalen-4-yl)dimethylamine (MonoPhos).

Preferably the chiral ligand is the commercially available Taniaphos-ligand (S)-1-dicyclohexylphosphino-2-[(S)-α-(dimethylamino)-2-(dicyclohexylphosphino)benzyl]-ferrocene.

Suitable non chiral ligands are dienes, amines, alcohols or phosphines.

If the chiral catalyst is prepared beforehand or in situ, the amount of chiral ligand is between 0.25 and 6 mol equivalents compared to the mol amount of metal precursor, preferably between 0.5 and 2 mol equivalents.

An additive is a compound added to the reaction mixture to enhance the hydrogenation rate, and/or increase the enantioselectivity. Suitable additives are organic and inorganic compounds, for example halogens (e.g. iodine), halogen containing compounds, bases, or acids. Suitable examples are iodine, potassium tert-butoxide, phthalimide, acetic acid or benzoic acid. Preferably 12 is used as additive in combination with an Ir-based chiral catalyst.

The amount of additive used in the preparation of the chiral hydrogenation catalyst of the invention is depending on the additive used, but is in general between 0.2 and 100 equivalents compared to the mol amount of metal used, preferably the amount of additive is between 1 and 50 mol equivalents, most preferably the amount of additive is between 1 and 10 mol equivalents compared with the mol amount of metal used.

The preferred chiral catalyst of the invention is prepared from a suitable Ir-precursor, the TaniaPhos ligand described above, and iodine as additive. The preferred amount of TaniaPhos ligand, is between 0.5 and 1.5 mol equivalents compared to the mol amount of Ir and the preferred amount of 12 (as additive) is between 1 and 3 mol equivalents compared to the mol amount of Ir. In a further embodiment of the invention the molar ratio between Ir and the chiral ligand is between 0.5:1 and 1:0.5.

Any solvent could be used for the hydrogenation reaction. Preferred are polar solvents, for example isopropanol, methanol, ethylacetate, MIBK, dichloromethane, and toluene, or any combination thereof.

The amount of catalyst compared with the amount of substrate is preferably as low as possible. In practice molar substrate catalyst ratio's are exceeding 100, and more preferably are exceeding 500 or 1000.

In one aspect of the invention, the hydrogenation catalyst is prepared beforehand, by mixing the metal precursor, the chiral ligand or chiral ligands or mixture of ligands, in a suitable solvent and optionally an additive.

The preparation of the catalyst is preferably done in a polar solvent. A suitable solvent is methanol, dichloromethane or a mixture of methanol and dichloromethane (notably dichloromethane).

The catalyst preparation is carried out at a reaction temperature between −10° C. and 80° C., preferably between 10° C. and 50° C. and more preferably between 15° C. and 25° C.

After preparation of the catalyst, the solution as such is added to the substrate solution, or the solvent used for the catalyst preparation is first evaporated and the catalyst is dissolved in the solvent of choice for the hydrogenation.

The preferred chiral catalyst of the invention is prepared beforehand from a suitable Ir-precursor, the TaniaPhos ligand described above, and iodine as additive in dichloromethane as solvent. The amount of TaniaPhos ligand is between 0.5 and 1.5 mol equivalents compared to the mol amount of Ir and the amount of I2 (as additive) is between 1 and 3 mol equivalents compared to the mol amount of Ir.

The hydrogenation is carried out with a transfer hydrogenation compound, for example isopropanol, or in the presence of hydrogen gas. Suitable hydrogen pressures are between 1 and 200 bar, preferably between 1 and 50 bar and more preferably between 1 and 10 bar.

The hydrogenation reaction is carried out at a temperature between −10° C. and 100° C., preferably between 10° C. and 75° C. and more preferably between 15 and 35° C. A temperature regime of first performing the hydrogenation at 15° C. and subsequent increase during hydrogenation increases the speed of conversion and ee of the product.

The technical advantages of step h, compared to the prior art, are the following:
Different chiral catalyst systems have been tested for the enantioselective hydrogenation of compound of formula 4. It has been found that only the Taniaphos catalyst shows a surprisingly high ee of 92-95%.
Compared to the racemic resolution, the novel enantioselective hydrogenation prevents the tedious separation of the enantiomers via diastereomeric salt formation and recycling of the wrong enantiomer.
Compared to the Noyori transfer hydrogenation catalyst, the enantioselective hydrogenation with the Taniaphos catalyst shows a surprisingly high ee of 92-95%.
Additionally, in large scale quantities, the enantioselective hydrogenation with the Taniaphos catalyst shows a more stable ee (as compared to the with the Noyori transfer hydrogenation catalyst).

In another aspect of the invention, the compound of formula 4*CH₃SO₃H is hydrogenated in the presence of a chiral catalyst and a solvent as described above, and in the presence of a base, and optionally in the presence of an additive as described above. In this aspect of the invention step g and step h are performed simultaneously.

Suitable bases for this aspect of the invention are any base compatible with the hydrogenation catalyst. Suitable bases are for example primary, secondary and tertiary amines, and compounds containing N,N-dialkylamine-groups, such as Et₃N, and iPr₂NEt. The amount of base may vary within a large range, preferably a catalytically amount of base is used, such as 0.1 equivalent compared with the compound of formula 4*CH₃SO₃H.

In step I of the reaction, the compound of formula 7 is reacted with acetic acid, to obtain the compound of formula 7*acetate.

The reaction is carried out in a suitable solvent, such as any aromatic solvent or mixture of aromatic solvents (such as benzene, toluene and/or xylene) and aliphatic hydrocarbons (preferably a C₄₋₈ aliphatic hydrocarbon, or any mixture thereof, or distillation fractions containing mainly heptane). A preferred solvent mixture is toluene and heptane with pure toluene and heptane or mixtures thereof. More preferred is a 4 to 1 mixture of toluene and heptane.

The reaction is carried out at a reaction temperature between −10 to 55° C. preferably between 0 and 20° C.

The reaction is carried out with 0.9 to 1.3 equivalents of acetic acid, more preferred with 1.0 equivalent of acetic acid.

Due to the unfavourable compound properties of enantiomeric 6,7-dimethoxy-1-[2-(4-trifluoromethyl-phenyl)-ethyl]-1,2,3,4-tetrahydro-isoquinoline hydrochloride, the enantiomeric pure synthesis is limited.

It was now surprisingly found that, the acetate salt of 6,7-dimethoxy-1-[2-(4-trifluoromethyl-phenyl)-ethyl]-1,2,3,4-tetrahydro-isoquinoline (compound 7*acetate) has improved compound properties, that enables the enantiomeric pure synthesis. Additionally, based on the improved compound properties of the compound 7*acetate a more complete crystallisation of the acetate salt is achieved, and therefore a higher yield is obtained.

The eutectics were surprisingly shifted by the choice of a suitable acid and solvent (aromatic solvent, e.g. toluene) towards the desired direction.

Reaction scheme 5:

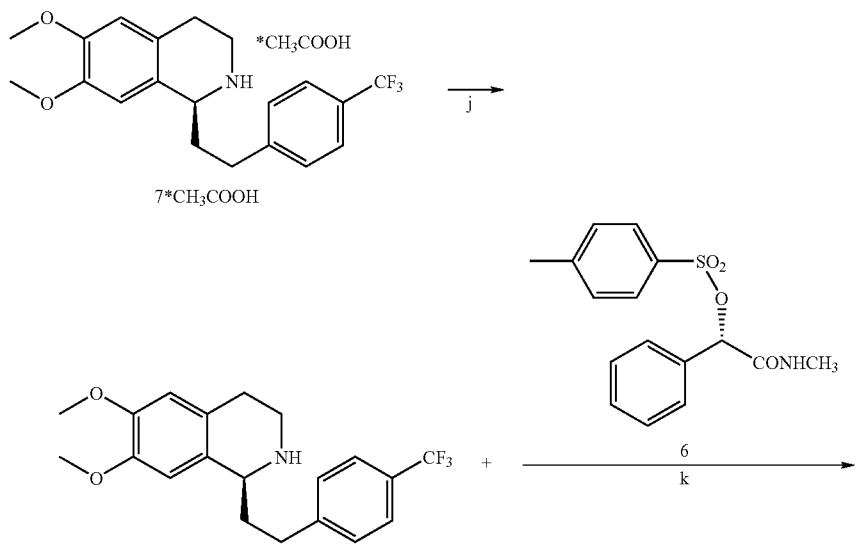

-continued

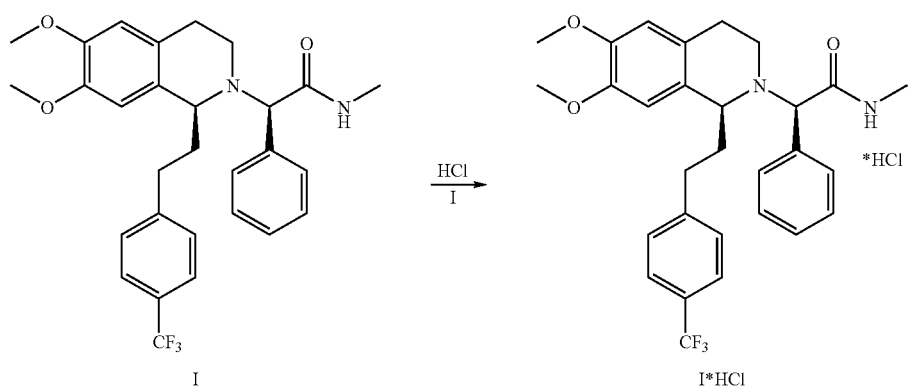

In step j of the reaction, the compound of formula 7*acetate is reacted with a base (preferably an inorganic base such as sodium hydroxide, more preferably an aqueous solution of sodium hydroxide) to obtain the compound of formula 7. In a preferred embodiment, the reaction is carried out with an aqueous solution of sodium hydroxide (preferably a sodium hydroxide solution which is 20%). Suitable solvents are ketones (such as acetone, ethyl methyl ketone, t-butyl methyl ether, $CH_2Cl_2$, MIBK, preferably MIBK). The reaction is carried out at a reaction temperature between 0-50° C., preferably between 15-25° C.

The technical advantage of step j, compared to the prior art, is e.g. the efficient use of MIBK as solvent.

In step k of the reaction, the compound of formula 7 is reacted with compound of formula 6, in the presence of a base to obtain the compound of formula 1. In a preferred embodiment, the reaction is carried out with 1.1-2.0 equivalents (preferably 1.2 equivalents) of compound of formula 6. Appropriate bases are $Li_2CO_3$, $Cs_2CO_3$, the corresponding bicarbonates, caustic soda, potassium carbonate, and mixtures thereof. In a preferred embodiment of the invention, mixtures of the before mentioned bases are used. In a further preferred embodiment, caustic soda is used in an amount of 0-2.2 equivalents (more preferred 1.2 equivalents of caustic soda), and potassium carbonate is used in an amount of 0-2.2 equivalents (more preferred 1.2 equivalents of potassium carbonate). Suitable solvents are MIBK, MTBE or $CH_2Cl_2$ (preferably MIBK). The reaction is carried out at a reaction temperature between 30-120° C., preferably between 70-90° C.

The technical advantage of step k, compared to the prior art, is that the coupling reaction could surprisingly be performed at higher concentrations.

In step l of the reaction, the compound of formula I is reacted with hydrochloric acid, to obtain compound of formula I*HCl. In a preferred embodiment, the reaction is carried out with 0.95-1.1 equivalents (preferably 1.0 equivalent) of aqueous hydrochloric acid.

The technical advantages of step l, compared to the prior art, are:

It is surprising that the HCl salt of the compound of formula I is obtained from compound of formula I in the presence of aqueous hydrochloric acid without significant amount of hydrolysis (hydrolysis less than 0.5%).

Furthermore the synthesis was simplified by the use of aqueous hydrochloric acid for the precipitation of the active pharmaceutical ingredient and subsequent azeotropic removal of water.

EXPERIMENTAL PART

Particular embodiments of the invention are described in the following examples, which serve to illustrate the invention in more detail without limiting its scope in any way.

Step 1: synthesis of 3-(4-trifluoromethyl-phenyl)-propionic acid (compound 1)

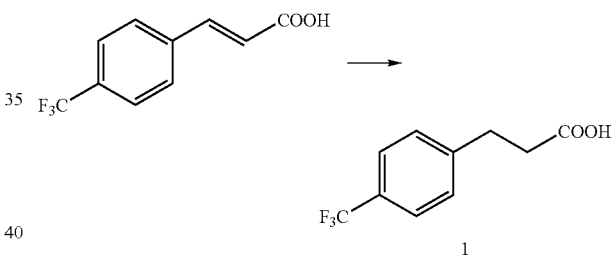

A solution of 4-trifluoromethylcinnamic acid (commercial available) in methanol is hydrogenated with Pd/C (5 wt %) at 2 bar until 4-trifluoromethylcinnamic acid has reacted completely. After removal of the catalyst by filtration the 4-trifluoromethylhydrocinnamic acid is further reacted in step 2 to compound 2.

Step 2: synthesis of 3-(4-trifluoromethyl-phenyl)-propionic acid methyl ester (compound 2)

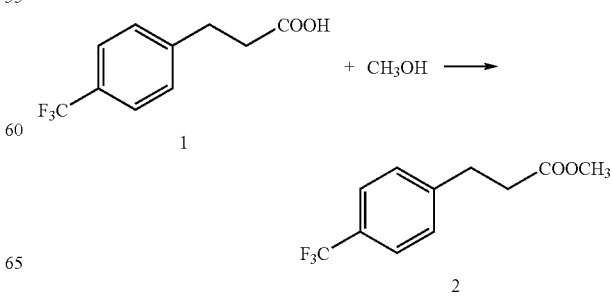

To the methanolic reaction mixture obtained from step 1 is added 5 mol % sulfuric acid and the mixture is heated. The formed water is distilled off until the esterification is complete. Then, methanol is completely removed.

Step 3: synthesis of N-[2-(3,4-dimethoxy-phenyl)-ethyl]-3-(4-trifluoromethyl-phenyl)-propionamide (compound 3)

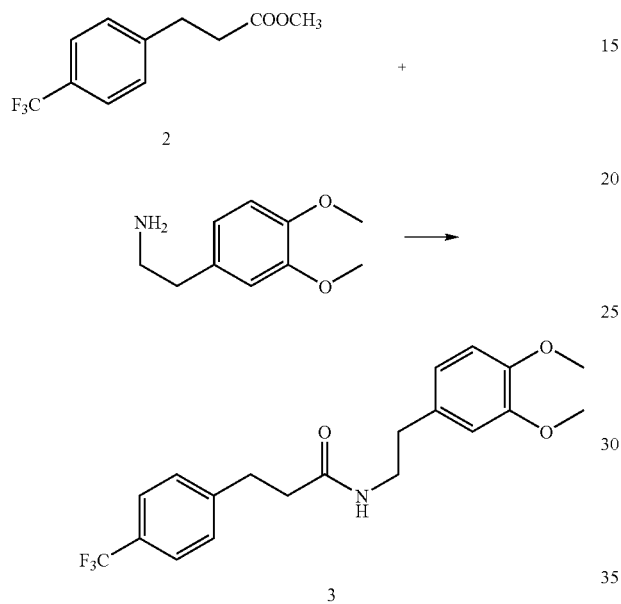

3-(4-trifluoromethyl-phenyl)-propionic acid methyl ester is dissolved in toluene, 1.05 equivalents 2-(3,4-dimethoxy-phenyl)-ethylamine (commercially available) and 1.1 equivalents sodium methoxide (30% in methanol) are added. At normal pressure the reaction mixture is heated to a maximum of 110° C. and methanol distilled until full conversion is reached. The reaction mixture is washed with water and sulfuric acid. During cooling of the organic phase, the compound 3 crystallises and is filtered, washed with cold toluene and dried in vacuo at 50° C.

Step 4: synthesis of 6,7-dimethoxy-1-[2-(4-trifluoromethyl-phenyl)-ethyl]-3,4-dihydro-isoquinoline methanesulfonic acid (compound 4*mesylate)

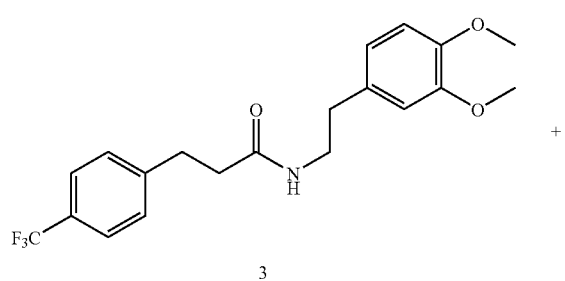

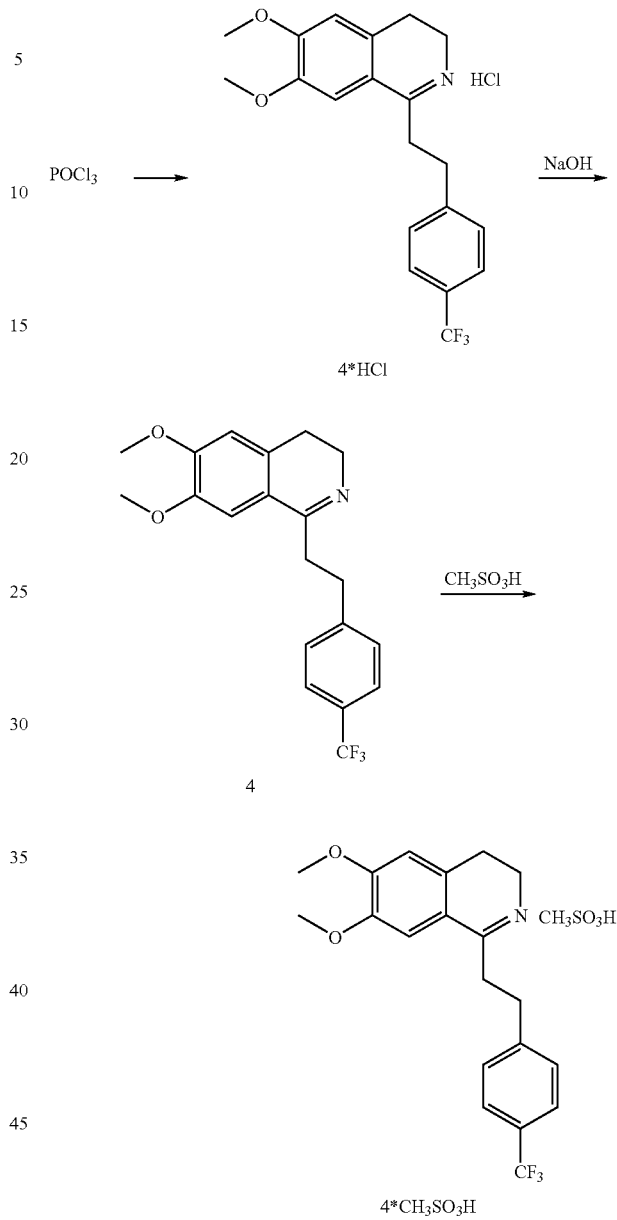

The compound 3 is suspended in toluene and heated to 80-100° C. After addition of 1.5 equivalents phosphorus oxychloride the mixture is heated for 6 hours to 80-100° C. and then cooled within 3 hours to 20° C. The suspension is added to water while maintaining the pH of the aqueous layer during addition and subsequent stirring between 7-8 by addition of a sodium hydroxide solution. The mixture is stirred until all precipitate is dissolved. After phase separation the water is removed by azeotropic distillation. Then 1.0 equivalent of methanesulfonic acid is added and the formed suspension stirred for some time. At this point in time parts of the solvent may be replaced by acetone, and then the mixture is slowly cooled to 0-10° C. and stirred at this temperature for another couple of hours. After filtration the product is washed with toluene and dried in vacuo.

Step 5: synthesis of (S)-mandelamid (compound 5)

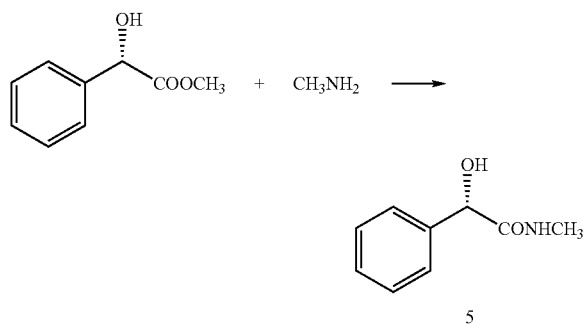

To a solution of methylamine (40% in water, 3.8 equivalents) is added, at ambient temperature, methyl (S)-mandelate (1.0 equivalent; commercially available), while keeping the temperature below 30° C. and stirred at ambient temperature until full conversion is achieved. Excess methylamine is removed by azeotropic distillation. Alternatively, after neutralisation with aqueous hydrochloric acid the aqueous solution is saturated with sodium chloride and extracted several times with dichloromethane. The organic layers are combined and the water is removed by azeotropic distillation.

Step 6: synthesis of (S)-toluene-4-sulfonic acid methylcarbamoyl-phenyl-methyl ester (compound 6)

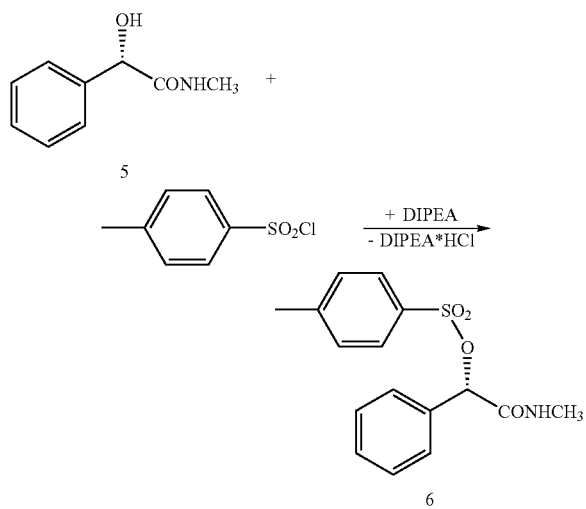

To the solution of mandelic acid amide in dichloromethane is added N-ethyldiisopropylamine (1.1 equivalents) at RT. Subsequently p-toluene sulfonic acid chloride (1.0 equivalent) is added keeping the temperature below 25° C. The reaction mixture is stirred at RT until a satisfactory conversion is reached and then washed with saturated sodium bicarbonate solution und water. After a solvent switch to ethyl acetate the solution is concentrated, cooled to −2° C. and the precipitate filtered. The crystals are washed with cooled ethyl acetate and dried in vacuo at 40° C.

Alternatively, to the solution of mandelic acid amide in dichloromethane is added 50% aqueous caustic soda at RT. Subsequently p-toluene sulfonic acid chloride (1.0 equivalent) is added as a solution in dichloromethane keeping the temperature below 25° C. The biphasic reaction mixture is stirred at RT until a satisfactory conversion is reached, phases are separated, the aqueous phase is extracted once with dichloromethane and then the combined organic phases are washed with water. After a solvent switch to toluene the solution is concentrated, cooled to 5° C. and the precipitate filtered. The crystals are washed with cooled toluene and dried in vacuo at 40° C.

Step 7: synthesis of 6,7-dimethoxy-1-[2-(4-trifluoromethyl-phenyl)-ethyl]-3,4-dihydro-isoquinoline (compound 4)

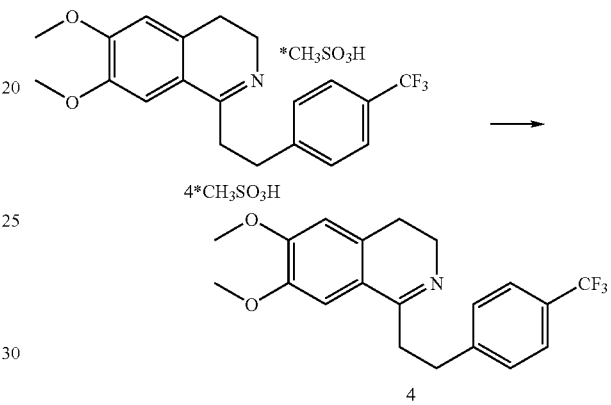

Method A:

To a suspension of 4*mesylate in ethyl acetate is added sodium hydroxide solution and stirred at RT until the precipitate is dissolved. After phase separation the aqueous phase is extracted a second time with ethyl acetate. The combined organic extracts are treated with charcoal and filtered. After removal of the water by azeotropic distillation the solution is diluted with ethyl acetate to a concentration of 5-6%.

Method B:

4*mesylate is added to a mixture of water and a 4:1 mixture of toluene/heptane (or, alternatively, to a mixture of water and toluene). The system is stirred until solids are dissolved. Aqueous caustic soda is then added, the mixture is stirred at RT, and phases are separated. The organic layer is washed several times with water and aqueous streams are discarded. Charcoal is charged to the solution of free imine 4, stirred, and the mixture is dried by azeotropic distillation. After removal of the water, the charcoal is removed by filtration, and the concentration of the solution is adjusted to 10-15%.

Method C:

To 4*mesylate (51.9 g; 0.113 mol) is added water (110 mL). The mixture is stirred for 30 min and toluene (500 mL) is added. Aqueous caustic soda (20 wt %; 110 mL) is then added. Toluene (600 mL) is then added and the phases are separated. The organic layer is washed four times with water (110 mL) and aqueous streams are discarded. The pH value of the aqueous phase should in the end be 7. Charcoal (Norix® SX Plus; 1.61 g) is added to the solution of free imine 4 which is then stirred for 1 h at RT. After filtration, the organic phase is washed with toluene (550 mL) and concentrated to a volume of 200-300 mL (70 mbar, 40° C.). Toluene (100 mL) is added and the organic phase is concentrated to a volume of about 120 mL (70 mbar, 40° C.). The appropriate volume of toluene to obtain the desired concentration of imine 4 is added and Ar is then bubbled through the imine solution for 30 min.

Step 8: synthesis of (1S)-6,7-dimethoxy-1-[2-(4-trifluoromethyl-phenyl)-ethyl]-3,4-dihydro-1H-isoquinoline (compound 7)

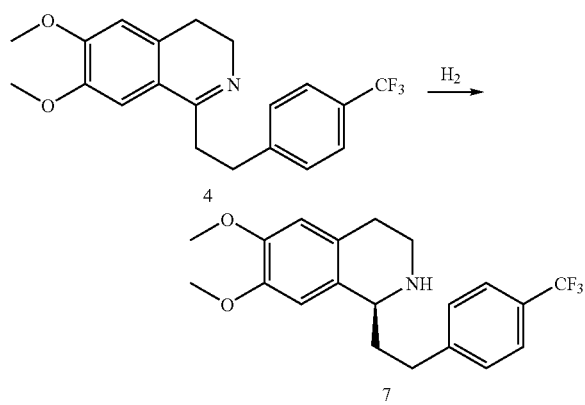

Taniaphos Ligand:

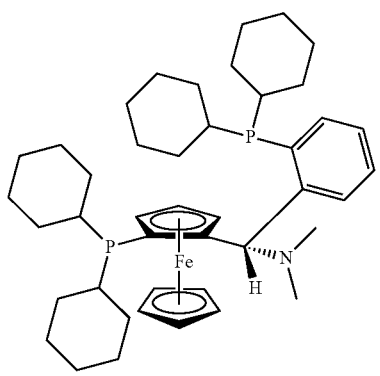

Method A:

To a solution of bis[chloro-1,5-cyclooctadiene-iridium] (commercially available) in degassed dichloromethane is added at 20° C. (S)-1-dicyclohexylphosphino-2-[(S)-α-(dimethylamino)-2-(dicyclohexylphosphino)benzyl]-ferrocene (the Taniaphos-ligand is commercially available or may be synthesized according to *Angew. Chem. J. Int. Ed*. (1999), 38, 3212). Subsequently a solution of iodine in degassed dichloromethane is added and the resulting solution is stirred until the formed precipitate is dissolved. The solution of the catalyst precursor is added to the imine solution of step 7 and hydrogenated at 5 bar H$_2$ pressure and 30° C.

Examples 1-6

Made According to Method A

| Ex. No. | I$_2$/Ir | Substrate/Catalyst | Conversion [%] | ee [%] |
|---|---|---|---|---|
| 1 | 1 | 200 | 99 | 73 |
| 2 | 1 | 20 | 100 | 89 |
| 3 | 2 | 200 | 100 | 95 |

-continued

| Ex. No. | I$_2$/Ir | Substrate/Catalyst | Conversion [%] | ee [%] |
|---|---|---|---|---|
| 4 | 2 | 20 | 100 | 95 |
| 5 | 4 | 200 | 100 | 86 |
| 6 | 4 | 20 | 100 | 92 |

Further experiments have been carried out at I$_2$/Ir ratio of 2 with increasing substrate to catalyst ratio (from 300 to 750), and the ee's remain between 94 and 95%.

Various other transition metal/chiral ligand systems in different solvents (such as HOAc, MeOH, DCM, IPA, toluene, Ac$_2$O, EtOAc, CH$_3$CN, MTBE, 2-butanone, DMF or DCM/HOAc (50:1)) have been tested to convert the compound of formula 4 into the compound of formula 7 via enantioselective hydrogenation. Transition metals tested include Ir (e.g. in the form of [Ir(COD)Cl]$_2$), and Rh (e.g. in the form of [Rh(COD)$_2$BF$_4$). For example the following chiral ligands have been tested:

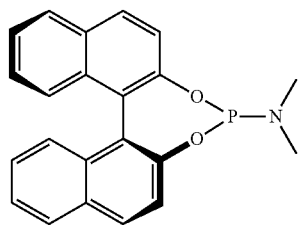

A

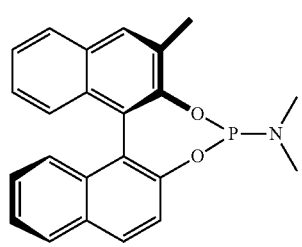

B

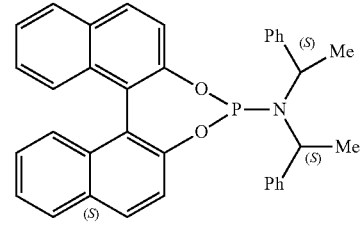

C

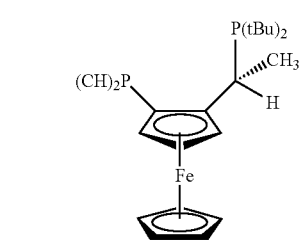

D

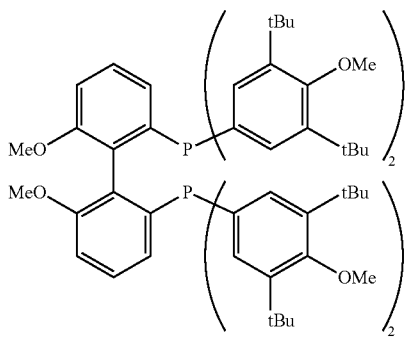

E

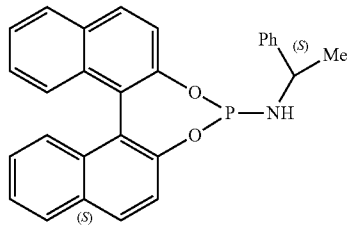

F

With the above mentioned transition metal/chiral ligand systems, the combination of high ee's in combination with high conversion rates could not be achieved.

Method B:

To a solution of bis[chloro-1,5-cyclooctadiene-iridium] (commercially available) in a degassed mixture of dichloromethane and methanol is added at 20° C. (R)-1-dicyclohexylphosphino-2-[(S)-α-(dimethylamino)-2-(dicyclohexylphosphino)benzyl]-ferrocene (the Taniaphos-ligand is commercially available or may be synthesized according to *Angew. Chem. J. Int. Ed.* (1999), 38, 3212). Subsequently, a solution of iodine in a degassed mixture of dichloromethane and methanol is added and the resulting solution is stirred until the formed precipitate is dissolved. The solution of the catalyst preparation is added to the imine solution of step 7, METHOD B, and hydrogenated at 5 bar (3-10 bar) $H_2$ pressure and at 20° C. (10-30° C.).

Examples 7-8

Made According to Method B

| Ex. No. | $I_2$/Ir | Solvent system for the compound 4 | Substrate/ Catalyst | Conversion [%] | ee after reaction [%] | ee after work-up [%] |
|---|---|---|---|---|---|---|
| 7 | 2 | toluene/heptane 4:1 | 1500 | 98 | 91 | 99 |
| 8 | 2 | toluene | 1500 | 98 | 88 | 99 |

Further experiments have been carried out at $I_2$/Ir ratio of 2 with increasing substrate to catalyst ratio (from 1000 to 2000), and typical ee's are between 88 and 95%.

Method C:

To bis[chloro-1,5-cyclooctadiene-iridium] (commercially available; 13.5 mg; 0.02 mmol) is added (R)-1-dicyclohexylphosphino-2-[(S)-α-(dimethylamino)-2-(dicyclohexylphosphino)benzyl]-ferrocene (30.5 mg; 0.042 mmol; the Taniaphos-ligand is commercially available or may be synthesized according to *Angew. Chem. J. Int. Ed.* (1999), 38, 3212). The mixture is placed under high vacuum conditions (1-2 mbar), then put under argon atmosphere (1 bar), this procedure (vacuum then argon atmosphere) being repeated 4 times. The mixture is kept under argon atmosphere and degassed methanol is added. After three hours stirring at RT, a red clear solution is obtained. Solid iodine is added and the resulting solution is stirred for 30 min. The solvent is then removed (1 mbar, RT) and the solid residue is dried for 30 min (1 mbar, RT). 1,2-dichloroethane (DCE) is added to the solid under argon, yielding the catalyst solution. Depending on the reaction solvent system, the solution of imine 4 (obtained at step 7, METHOD C) in toluene (Tol) is mixed with the appropriate volume of hexane (Hex), heptane (Hept) or tetrahydrofuran (THF) and the catalyst solution in DCE previously obtained is added. The volume of Tol used for the imine 4, the volume of DCE used for the catalyst solution and the volume of hexane (Hex), heptane (Hept) or tetrahydrofuran (THF) added are such that they make together the reaction solvent system. The reaction mixture is put under $H_2$ pressure (5 bar) at the temperature T, the reaction being completed after a certain time $t_R$. Details of the various experiments carried out are summarized in the table hereafter.

Examples 9-17

Made According to Method C

| Ex. No. | Quantity of imine 4 [mmol] | Reaction solvent system | Solvent volume [mL] | $I_2$/Ir ratio [eq./eq.] | T [° C.] | Substrate/ Catalyst | Conversion [%] | ee [%] | $t_R$ [min] |
|---|---|---|---|---|---|---|---|---|---|
| 9[a,b] | 7.5 | Tol/THF/DCE 9/2/1 | 24 | 3 | RT | 1000 | 100 | 97 | 30 |
| 10[a] | 7.5 | Tol/Hex/DCE 9/2/1 | 24 | 3 | RT | 2000 | 99 | 95 | 15 |
| 11[c] | 10 | Tol/THF/DCE 9/2/1 | 24 | 4 | RT | 2000 | 94 | 95 | 120 |
| 12 | 11.3 | Tol/Hex/DCE 9/2/1 | 28 | 3 | 16 | 3000 | 99.5 | 96 | 90 |
| 13 | 11.3 | Tol/Hex/DCE 9/2/1 | 28 | 3 | 16 | 4000 | 95 | 95 | 80 |
| 14 | 19 | Tol/Hex/DCE 9/2/1 | 85 | 3 | 16 | 3000 | 99.3 | 95.7 | 45 |
| 15 | 11.3 | Tol/Hex/DCE 9/2/1 | 27 | 3 | 16 | 4000 | 95.6 | 95.3 | 150 |

-continued

| Ex. No. | Quantity of imine 4 [mmol] | Reaction solvent system | Solvent volume [mL] | I₂/Ir ratio [eq./eq.] | T [° C.] | Substrate/ Catalyst | Conversion [%] | ee [%] | $t_R$ [min] |
|---|---|---|---|---|---|---|---|---|---|
| 16[d] | 38 | Tol/Hex/DCE 9/2/1 | 91 | 3 | 16 | 2500 | 100 | 95.2 | 29 |
| 17 | 38 | Tol/Hept/DCE 13/4/1 | 119 | 3 | 16 | 3000 | 98.8 | 95.0 | 60 |

[a]For this experiment, the imine 4 was prepared using the protocol of step 7, METHOD B, the imine solution being however dried by the use of Na₂SO₄
[b]In this experiment, the catalyst was stirred with methanol for one hour only (not three).
[c]In this experiment, after the methanol removal from the catalyst, toluene was added to the catalyst which was then removed
[d]In this experiment, the catalyst was stored one day after its preparation before being used Step 7 and 8 simultaneously.

To a suspension of 4*mesylate in ethyl acetate is added bis[chloro-1,5-cyclooctadiene-iridium], a suitable amount of the ligand B as depicted above, and iPr₂NEt. The mixture is warmed to 50° C., and 25 bar of H₂ pressure is applied.

Step 9: synthesis of (1S)-6,7-dimethoxy-1-[2-(4-trifluoromethyl-phenyl)-ethyl]-3,4-dihydro-1H-isoquinoline acetic acid (compound 7*acetic acid)

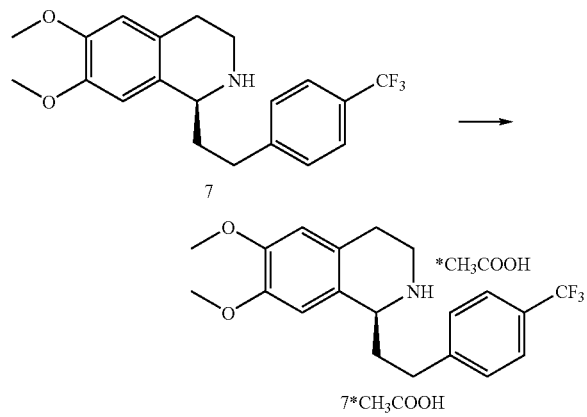

Method A:

After full conversion a solvent switch to toluene is performed. Then heptanes are added to reach a ratio of toluene/heptanes of 4 to 1. By addition of 1.0 equivalent of acetic acid compound 7*acetic acid is precipitated at 20° C. The suspension is aged at RT to ensure complete precipitation, filtered and washed with heptanes. The product is dried in vacuo at 40° C.

Method B:

After full conversion, the residual solvents dichloromethane and methanol from the catalyst preparation are removed by distillation, resulting in a solution of amine 7 in toluene, respectively a toluene/heptane mixture. By addition of 1.0 equivalent acetic acid, compound 7*acetic acid is precipitated at 20° C. The suspension is aged at RT (0-20° C.) to ensure complete precipitation, filtered and washed with toluene, respectively a mixture of toluene/heptanes. The product is dried in vacuo at 40° C. By application of this method the optical purity of the product can be increased even from 81% ee after hydrogenation up to 99% ee in the isolated material.

Step 10: synthesis of (1S)-6,7-dimethoxy-1-[2-(4-trifluoromethyl-phenyl)-ethyl]-3,4-dihydro-1H-isoquinoline (compound 7)

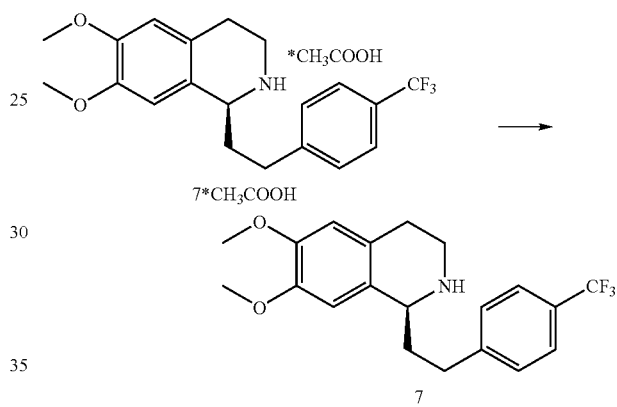

To a suspension of compound 7*acetic acid in MIBK is added sodium hydroxide solution (20%) and stirred at RT until the precipitate is dissolved. After phase separation, the organic layer is washed with water. After removal of the water from the organic phase by azeotropic distillation, the solution is diluted with MIBK to a concentration of 9-16%.

Step 11: synthesis of (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (compound I)

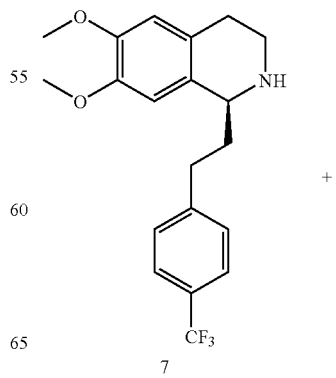

+

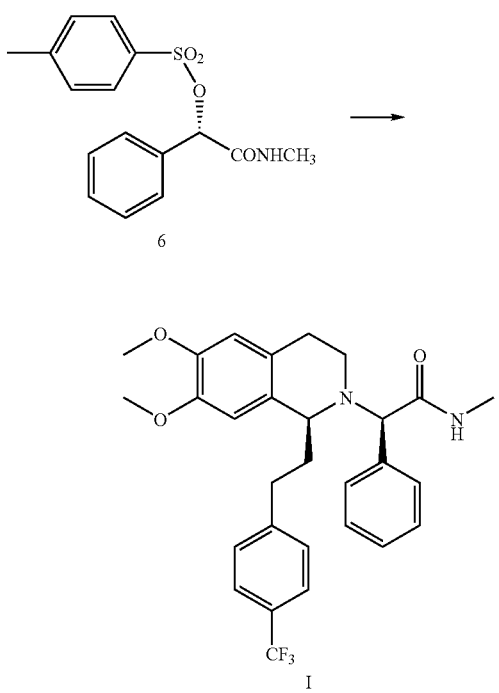

To the solution of the compound 7 in MIBK are added 1.2 equivalents of the compound 6, 1.1 equivalents caustic soda and 1.1 equivalents potassium carbonate and heated to 70-90° C. Water is added and the mixture is heated at the same temperature for 0.5 to 3 hours and then cooled to RT. Alternatively, after full conversion the solution is cooled to RT and water is added. Phase separation is followed by a second washing of the organic phase with water and again phase separation.

Step 12: synthesis of (2R)-2-(1S)-6,7-dimethoxy-1-[2-(4-trifluoromethyl-phenyl)-ethyl]-3,4-dihydro-1H-isoquinolin-2-yl)N-methyl-2-phenyl-acetamide hydrochloride (compound I hydrochloride)

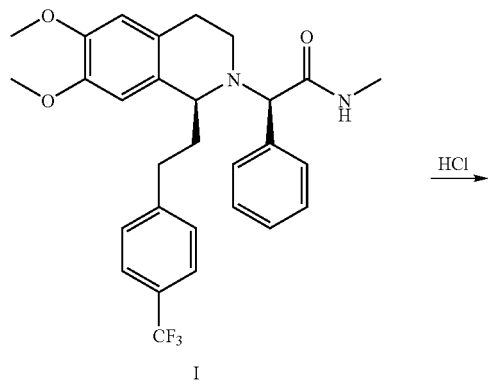

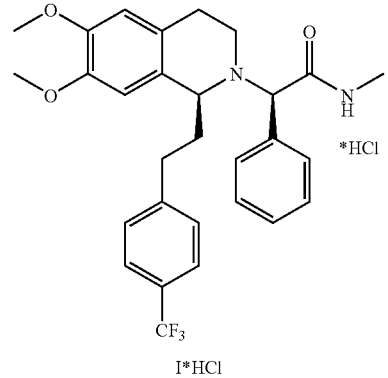

To the organic phase of step 11 is added 1 equivalent aqueous hydrochloric acid and then the water removed by azeotropic distillation in vacuo.

Then, either:

The precipitate is dissolved by addition of 2-propanol at 75° C. Concentration of the solution leads to crystallisation and the suspension is then cooled to RT. To ensure complete crystallisation, the suspension is aged at RT, then filtered and washed with a MIBK-2-propanol mixture.

or:

the compound I*HCl is obtained by crystallization from the organic phase of step 11 (MIBK) containing an adjusted amount of residual water (0.4-1.5%, e.g. 0.7%) without using 2-propanol at a temperature of above 40° C. (e.g. about 65° C.) using seeding crystals.

The product is isolated e.g. on an inverting bag centrifuge and dried in vacuo at 50° C.

The invention claimed is:

1. Compound of formula 7*acetate

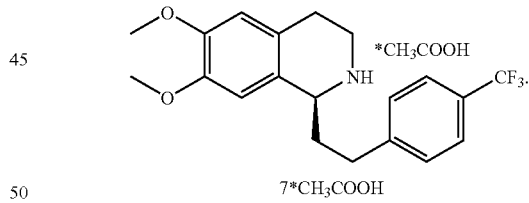

2. Process for the preparation of the compound of formula 7*acetate

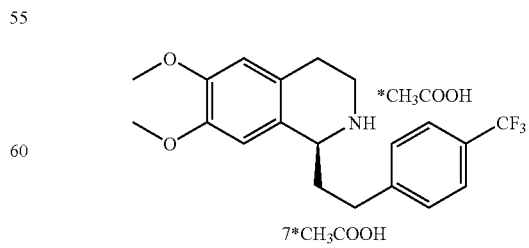

which process comprises the reaction of the compound of formula 7

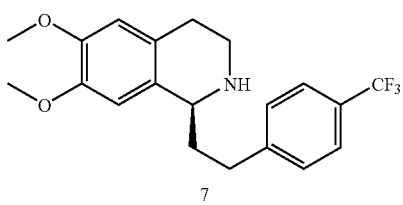

7 with acetic acid, to obtain the compound of formula 7*acetate.

3. Process according to claim 2, for the preparation of the compound of formula 7*acetate, wherein the compound of formula 7

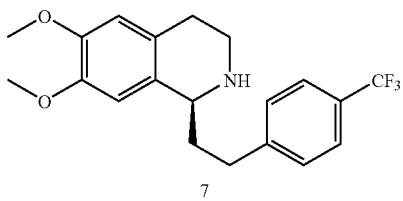

7 is prepared by hydrogenation of the compound of formula 4

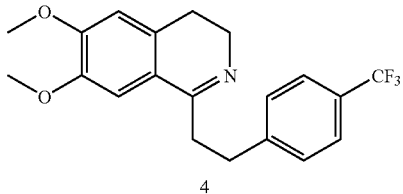

4 in the presence of bis[chloro-1,5-cyclooctadiene-iridium], (S)-1-dicyclohexylphosphino-2-[(S)-α-(dimethylamino)-2-(dicyclohexylphosphino)benzyl]-ferrocene, iodine and a solvent, under hydrogen pressure of 1-200 bar, to obtain the compound of formula 7.

4. Process according to claim 3, for the preparation of the compound of formula 7*acetate, wherein the compound of formula 4

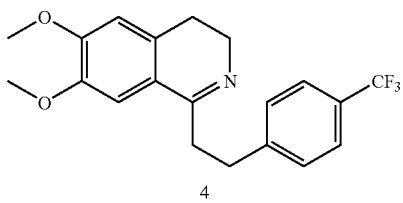

4 is prepared by reaction of the compound of formula 4*mesylate

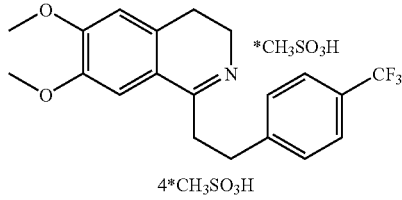

4*CH₃SO₃H with a base, to obtain the compound of formula 4.

5. Process according to claim 2, wherein the reaction is carried out with 0.9 to 1.3 equivalents of acetic acid.

6. Process according to claim 3, wherein the amount of iodine compared to the amount of Ir is between 0.2 and 10 mol equivalents.

7. Process according to claim 3, wherein the molar ratio between Ir and the chiral ligand is between 0.5:1 and 1:0.5.

8. Process according to claim 3, wherein the hydrogen pressure is between 1 and 50 bar.

9. Process according to claim 4, wherein the amount of base is between 0.9 and 1.5 mol equivalents.

10. A process for the preparation of compound of formula I*HCl

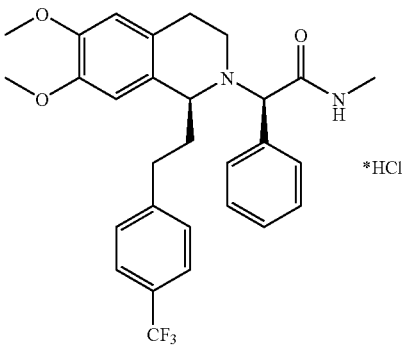

I comprising:
a) reacting the compound of formula 7*acetate,

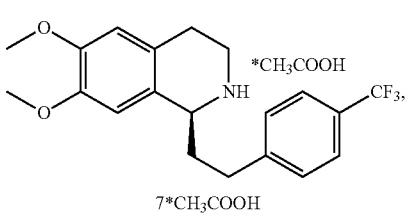

7*CH₃COOH with a base to obtain the compound of formula 7:

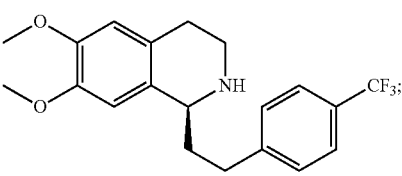

7 b) reacting the compound of formula 7 with compound of formula 6:
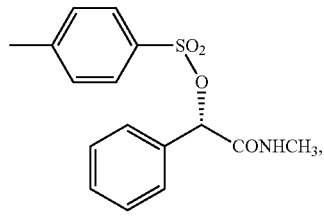
in the presence of a base, to obtain the compound of formula I:
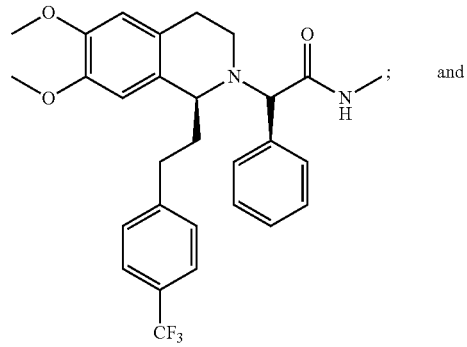
c) reacting the compound of formula I with hydrochloric acid, to obtain the compound of formula I*HCl.
* * * * *